US00PP10484P

United States Patent [19]

Lemon

[11] Patent Number: Plant 10,484

[45] Date of Patent: Jul. 7, 1998

[54] VARIETY OF GERANIUM PLANT NAMED 'PATRIOT LIGHT PINK'

[75] Inventor: David Lemon, Lompoc, Calif.

[73] Assignee: John Bodger & Sons Company, So. El Monte, Calif.

[21] Appl. No.: 724,702

[22] Filed: Oct. 1, 1996

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 8,552 1/1994 Trees ..... Plt./87.12

P.P. 9,729 12/1996 Dümmen ..... Plt./87.12

*Primary Examiner*—Howard J. Locker

*Attorney, Agent, or Firm*—Fulwider Patton Lee & Utecht, LLP

[57] ABSTRACT

The cultivar is characterized by its medium green foliage and pale pink bloom. Its strong growth habit, quick rooting time and continuous flowering provide for superb cuttings and also for quick recovery following wet weather conditions. The blooms exhibit good post-harvest quality. Patriot Light Pink performs very well either indoors or outdoors.

2 Drawing Sheets

BACKGROUND OF THE NEW PLANT

The present invention comprises a new and distinct cultivar of *Pelargonium×hortorum* known by the varietal name Patriot Light Pink (Oglevee No. 1305, Bodger No. 1GM 180-7). The new variety was discovered in a selective breeding program by David Lemon at Bodger Seeds, Ltd., Lompoc, Calif. The new variety is a selection from the crossing of Aphrodite (unpatented) which is characterized by a white flower over medium green foliage, with Bodger No. 1 GM 4 (unpatented) which has a lavender pink flower marked with some white and dark pink veins and further having dark green foliage, while the claimed cultivar has an apple blossom pink flower with a white eye and dark pink veins over medium green foliage.

The new cultivar was first asexually reproduced by cuttings at Oglevee Ltd., Connellsville, Pa., and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa., using full light, 60° Fahrenheit night temperature, 68° Fahrenheit day temperature, 72° Fahrenheit vent temperature and grown in a soilless media of constant fertilizer 200–250 parts per million of nitrogen and potassium has a response time of six weeks from the rooted cutting to a flowering plant in a 10.0 cm pot.

DESCRIPTION OF THE DRAWINGS

The accompanying drawings illustrate the new cultivar, the colors depicted being as nearly true as possible with color illustrations of this type.

Sheet 1 represents a side view of the new cultivar.

Sheet 2 is a top view.

DESCRIPTION OF THE NEW PLANT

The following detailed description sets forth characteristics of the new cultivar. The data which defines each characteristics was collected from asexual reproductions carried out by Oglevee Ltd. in Connellsville, Pa. The plant histories were taken on rooted cuttings believed to have been potted on approximately Feb. 1, 1996 and flowering on approximately Mar. 14, 1996 under full light and greenhouse, and colorings were taken indoors under 200–220 foot candles of fluorescent cool white light using the R.H.S. Colour Chart of The Royal Horticultural Society of London.

The Plant

Classification:

*Botanical.*—*Pelargonium×hortorum.*

*Commercial.*—*Florist's Geranium Patriot Light Pink* (Florist's geraniums are a high quality plant which also grows well outdoors).

Form: Semi-dwarf mound.

*Height.*—20–33 cm above media.

*Growth.*—Free basal branching.

*Strength.*—No artificial support needed.

Foliage: Stalked leaf attachment.

Leaves:

*Size.*—8–10.5 cm across.

*Shape.*—Reniform; cordate base.

*Margin.*—Crenate.

*Texture.*—Smooth, pubescent, slightly reflective.

*Color.*—Top: Green group 137A at outer edge to green group 137C near center. Bottom: Yellow-green group 147B. Zone: None prominent; leaf zone presence is not distinct from a distance, however, variation in the depth of color where the zone typically occurs, is present.

*Ribs and veins.*—Palmate venation: Color: Yellow-green group 144B.

Petioles:

*Length.*—6.0–7.2 cm.

*Color.*—Yellow-green group 144B.

Stem:

*Color.*—Yellow-green group 144B.

*Internodes.*—1.8–3.0 cm.

The Bud (Umbel)

Shape: Upright, hemispherical cluster.

Size: 3.5–4.0 cm across.

Inflorescence

Blooming habit: continuous, free and early flowing.

Borne: Floret on pedicel; pedicel and peduncle 8–12 cm above foliage.

Closed florets:

*Bud size.*—(1.1×0.6) to (1.6×0.8) cm; showing color.

*Size.*—Fully open bloom: 7.0–10.0 cm across.

Open florets:

*Form.*—Semi-double (these plants typically have 5–6 petals plus 3–8 petaloids which form a semi-double floret), open and flat to slightly cupped; 38 florets per inflorescence appearing.

*Color.*—Top: Overall shade is red-purple group 73C with slight veining of red-purple group 68C from the center of floret that fades into the red-purple group 73C. Bottom: Veins of red group 55A running through a pale red-purple group 65D. Eye: White group 155D with white group 68C veins in white eye which seem to disappear into the petal color upper surface of petal.

*Petals.*—5–6 in number.

*Size.*—3.5–4.0 cm across.

*Texture and appearance.*—Delicate light pink flower on medium green foliage.

Petaloids:

*Quantity.*—3–8 (however petaloid number is highly variable with age of the plant and cultural conditions).

*Shape.*—Pinched; feathered; puckered (irregular) some almost having a petal shape but being distorted; some with anthers attached.

*Color.*—Top: Red-purple group 73C. Bottom: Red-purple group 65D with veins of red group 55A.

Pedicel:

*Length.*—2.3–2.9 cm in length.

*Color.*—Yellow-green group 145A; many with blush of greyed-purple group 183D; some have blush along entire pedicel, others more near floret.

Peduncle:

*Length.*—15–18 cm.

*Color.*—Yellow-green group 144A.

Persistence:

*Disease resistance.*—Not known.

*Lasting quality.*—Slow to shatter, holds up well outdoors.

Reproductive Organs

Stamens:

*Anthers.*—0.2 cm in length.

*Filaments.*—Length: 0.5–0.7 cm. Color: White.

*Pollen.*—Greyed-orange group 169A.

Pistils:

*Number.*—One.

*Length.*—0.8 cm in length.

*Stigma.*—4–5 parted. Color: Closed — outside color is red group 53C. Open — inner color is red group 51B.

*Style.*—Length: 0.5 cm.

Ovaries:

*Color.*—Green, superior, pubescent.

*Length.*—0.4 cm.

Fruit: None.

General Characteristics

Patriot Light Pink brings a new color to the current geranium market. The pale pink color is accented by the medium green foliage which creates an illusion of a zone when observed up close. Cutting production and rooting time is very quick. Both indoor and outdoor performance is exceptional.

I claim:

1. A new and distinct variety of Geranium plant, substantially as shown and described.

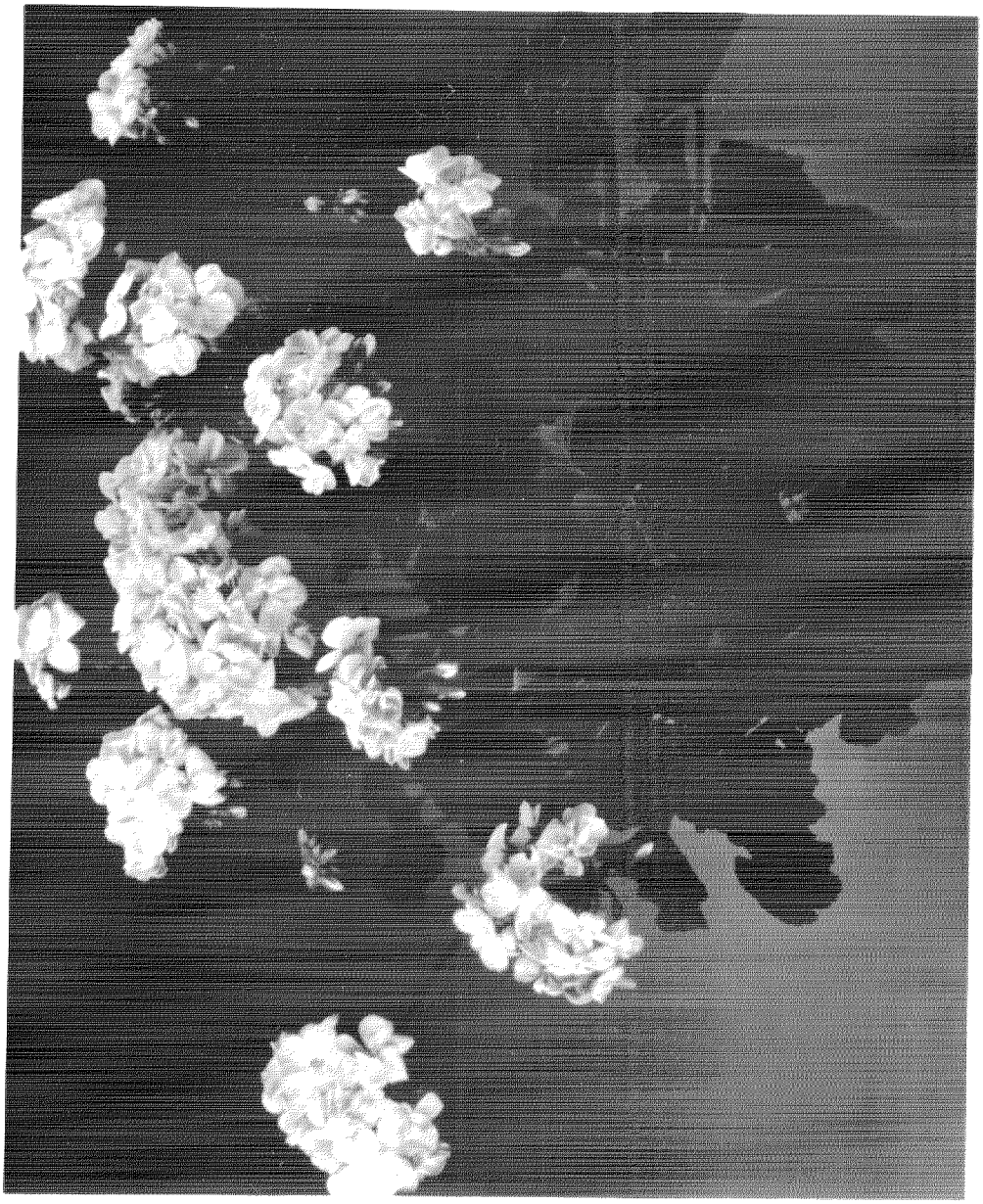

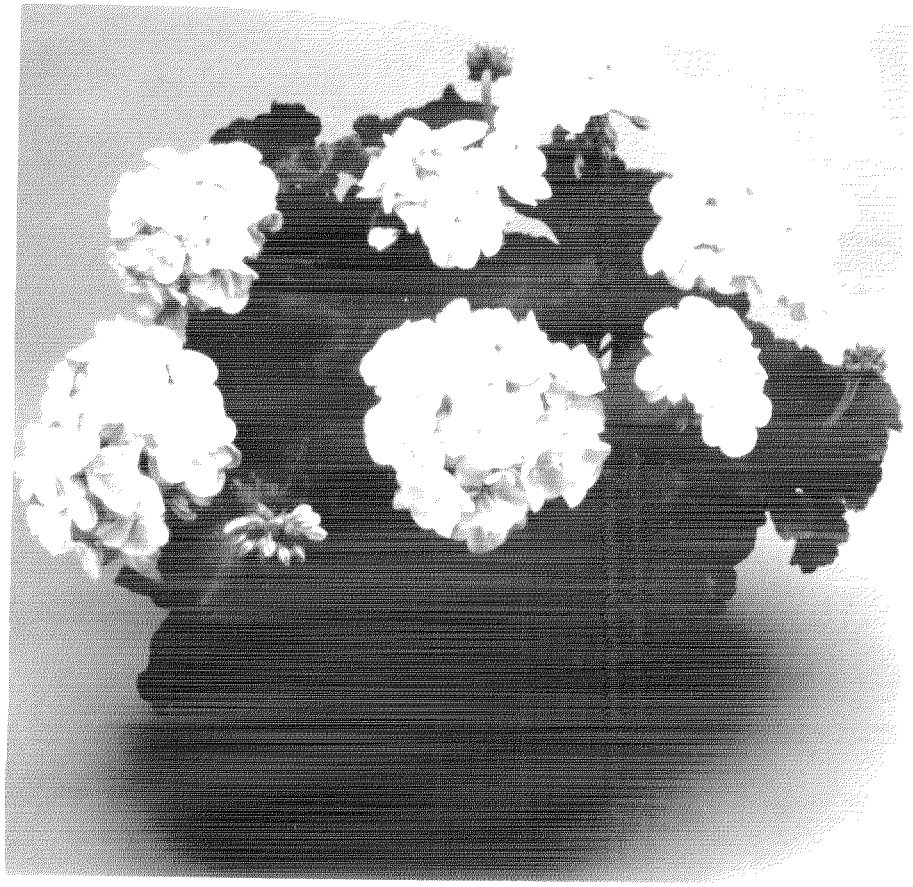

* * * * *